(12) United States Patent
Vitale et al.

(10) Patent No.: US 11,039,928 B2
(45) Date of Patent: *Jun. 22, 2021

(54) JOINT SURFACE REPLACEMENT SYSTEM

(71) Applicant: Accufix Surgical Inc., West Haven, CT (US)

(72) Inventors: Glenn C. Vitale, Milford, CT (US); Michael Parisi, Trumbull, CT (US); Wayne Conlan, West Haven, CT (US)

(73) Assignee: Accufix Surgical, Inc., West Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/137,695

(22) Filed: Dec. 30, 2020

(65) Prior Publication Data

US 2021/0113338 A1 Apr. 22, 2021

Related U.S. Application Data

(63) Continuation of application No. 17/093,891, filed on Nov. 10, 2020, now Pat. No. 10,959,851, which is a
(Continued)

(51) Int. Cl.
*A61F 2/42* (2006.01)
*A61F 2/30* (2006.01)
(Continued)

(52) U.S. Cl.
CPC ........ *A61F 2/30771* (2013.01); *A61F 2/4225* (2013.01); *A61F 2/4606* (2013.01); *A61B 17/1617* (2013.01); *A61B 17/1682* (2013.01); *A61F 2/30744* (2013.01); *A61F 2/4603* (2013.01); *A61F 2002/3082* (2013.01);
(Continued)

(58) Field of Classification Search
CPC ............ A61F 2/4225; A61F 2002/4233; A61F 2/4606; A61F 2002/4228; A61F 2002/4238; A61F 2002/30665; A61F 2002/30299; A61F 2002/3082; A61F 2002/30841; A61F 2/30771; A61F 2002/30873; A61F 2002/30904; A61F 2002/30827; A61F 2002/30894
See application file for complete search history.

(56) References Cited

U.S. PATENT DOCUMENTS 2,696,817 A 4/1952 Preveo
3,681,786 A 8/1972 Lynch
(Continued)

*Primary Examiner* — David H Willse
*Assistant Examiner* — Javier G Blanco
(74) *Attorney, Agent, or Firm* — DeLio Peterson & Curcio; Kelly M. Nowak

(57) ABSTRACT

The present invention relates to an articular joint replacement system. The system has first and second components. Each component has a tapered head piece for covering the end of a bone and for acting as an articular surface, an integrally formed screw stem having a length sufficient to extend into the medullary canal, and inwardly angled bone grips affixed to the underside of the head piece to allow solid fixation to the bone by compression press fit. The head piece of the first component is provided with a shaped exterior surface which complements the shaped exterior surface of the head piece of the second component and which allows motion in three planes.

18 Claims, 17 Drawing Sheets

Related U.S. Application Data continuation of application No. 17/006,133, filed on Aug. 28, 2020, which is a continuation of application No. 15/829,495, filed on Dec. 1, 2017, now Pat. No. 10,765,522.

(60) Provisional application No. 62/428,875, filed on Dec. 1, 2016.

(51) Int. Cl.
*A61F 2/46* (2006.01)
*A61B 17/16* (2006.01)

(52) U.S. Cl.
CPC ........... *A61F 2002/3085* (2013.01); *A61F 2002/3093* (2013.01); *A61F 2002/30176* (2013.01); *A61F 2002/30299* (2013.01); *A61F 2002/30378* (2013.01); *A61F 2002/30616* (2013.01); *A61F 2002/30654* (2013.01); *A61F 2002/30736* (2013.01); *A61F 2002/30841* (2013.01); *A61F 2002/30873* (2013.01); *A61F 2002/4233* (2013.01); *A61F 2310/00017* (2013.01); *A61F 2310/00023* (2013.01); *A61F 2310/00179* (2013.01)

(56) References Cited

U.S. PATENT DOCUMENTS

| | | | |
|---|---|---|---|
| 4,085,466 A | 4/1978 | Goodfellow et al. | |
| 4,355,429 A | 10/1982 | Mittelmeier et al. | |
| 4,462,120 A | 7/1984 | Rambert et al. | |
| 4,642,122 A | 2/1987 | Steffee | |
| 4,725,280 A | 2/1988 | Laure | |
| 4,759,768 A | 7/1988 | Hermann et al. | |
| 4,955,916 A | 9/1990 | Carignan et al. | |
| 5,007,932 A | 4/1991 | Bekki et al. | |
| 5,037,440 A | 8/1991 | Koenig | |
| 5,176,710 A | 1/1993 | Hahn et al. | |
| 5,207,712 A | 5/1993 | Cohen | |
| 5,683,466 A * | 11/1997 | Vitale | A61F 2/30756 623/21.15 |
| 7,678,151 B2 * | 3/2010 | Ek | A61B 17/1642 623/20.14 |
| 2007/0005143 A1 * | 1/2007 | Ek | A61F 2/389 623/20.32 |
| 2010/0268238 A1 * | 10/2010 | Sikora | A61F 2/30756 606/87 |

* cited by examiner

JOINT SURFACE REPLACEMENT SYSTEM

BACKGROUND OF THE INVENTION

1. Field of the Invention

The present invention relates to apparatus, systems and methods for replacing and/or repairing cartilaginous surfaces in a human joint.

2. Description of Related Art

The use of prosthetic devices to replace joints and various bone and cartilage structures in a human body is well known in the prior art. These devices have taken a wide variety of configurations and shapes which are often closely related to the particular joint or anatomical structure being replaced. Described below are some of the various devices shown in the patent literature.

U.S. Pat. No. 3,681,786 to Lynch, U.S. Pat. No. 4,725,280 to Laure, U.S. Pat. No. 4,759,768 to Hermann et al., U.S. Pat. No. 4,955,916 to Carignan et al., and U.S. Pat. No. 5,007,932 to Bekki et al. disclose prosthetic devices designed to replace human finger joints. These joint replacement devices include both single component apparatus and multi-component apparatus.

For instance, Lynch discloses a one-piece prosthesis formed from a single piece of flexible elastomeric, physiologically inert material and a polyester felt pad embedded within the prothesis. The felt pad has an exposed surface which provides for the ingrowth of body tissue. Laure discloses a prosthetic joint having a shell-like member secured to the distal end of one phalanx and a tack portion which extends into the other phalanx for replacement of either the proximal or distal phalangeal joint of the finger. Hermann discloses a prosthetic joint comprising two pins with articulation surfaces provided between the pins, whereby the pins are designed to be directly or indirectly inserted into a respective one of the two bones to be joined. The Carignan discloses a thumb joint prosthesis having tapered and threaded carpal and metacarpal components, whereby the carpal component has a U-shaped cavity containing a polyethylene insert that receives a tapered head received in a corresponding cavity within the metacarpal component. Bekki discloses a two-member prosthetic device where the first member has a convex curved surface and the second member has a concave curved surface which is in sliding contact with the convex curved surface.

Various patent literature is also directed to prosthetic devices designed to replace other human joints, such as, elbows, knees, toe joints, and the like. For instance, U.S. Pat. No. 2,696,817 to Prevo discloses a prosthetic elbow joint comprising two finned shafts insertable into the marrow cavities of the humerus and the ulna, which shafts are pivotally connected by a trunnion.

U.S. Pat. No. 4,355,429 to Mittlemeier et al., U.S. Pat. No. 4,462,120 to Rambert et al., U.S. Pat. No. 4,085,466 to Goodfellow et al. and U.S. Pat. No. 5,176,710 to Hahn et al. are directed to various knee prosthetic devices. Mittlemeier discloses a slide prothesis which includes a surface replacement for the knee cap having anchoring pins that are provided with a saw tooth-like or bone screw-shaped profile. Rambert discloses a total knee prosthesis having upper and lower support members provided with externally threaded, tapered shanks to which they are detachably secured, whereby the shanks are screwable into the medullary canals of the femur and the tibia. Goodfellow discloses a device having first and second components respectively providing convex and relatively flat articulatory bearing surfaces. Hahn discloses a prosthetic device made from materials having a low bulk modulus of elasticity.

Toe joint replacement systems have also been disclosed in the prior art. For instance, U.S. Pat. No. 4,642,122, to Steffee and U.S. Pat. No. 5,037,440 to Koening disclose devices for replacing a toe joint. The Steffee device comprises a one-piece tack member implantable into the distal end of a metatarsal and a one-piece socket member implantable into the proximal end of a phalanx. The tack member has an enlarged head defining a part-spherical convex surface which engages a part-spherical concave bearing surface on an enlarged head of the socket member. Koenig discloses a device that also includes a first member having a convex surface and a second member having a concave surface.

In addition to the patent literature, various commercial toe implants are currently on the market however many of these commercially available implants deteriorate, collapse, break and suffer torque deformation. Additionally, implantation of some devices require modifications to the sub-chondral bone. Still further, some devices require the use of silicone, silastics, glues, ingrowth jackets, and grommets. These disadvantages are overcome by the joint replacement apparatus, systems and methods of the present invention.

SUMMARY OF THE INVENTION

Accordingly, it is an object of the present invention to provide an improved joint surface replacement apparatus, system and methods.

It is a further object of the present invention to provide a joint surface replacement system that eliminates breakage, bulk and excessive weight—the major contributory factors which lead to destructive lateral shearing forces resulting in complete implant failure.

It is a further object of the present invention to provide a joint surface replacement system as above that provides a full range of motion in three planes.

It is still a further object of the present invention to provide a joint surface replacement system as above which is firmly anchored to bone.

It is yet a further object of the present invention to provide a relatively simple method for installing the joint surface replacement system of the present invention making it extremely cost effective.

The foregoing objects are achieved by the joint surface replacement system and the installation method of the present invention.

In accordance with the present invention, the joint surface replacement system of the present invention has two elements which are each implanted into one of the bones forming the joint. The two elements define the new joint surfaces. A first one of the elements has a partially spherical member for covering an end of a first one of the bones, a centrally located screw means formed integrally with the partially spherical member and a means for gripping the end of the first bone for allowing solid fixation by compression press fit. The second one of the elements has a structure substantially identical to that of the first one of the elements. It too has a partially spherical member for covering an end of the second bone, an integral screw means and a bone end gripping means. The second element differs from the first element only by the shape of the partially spherical member. The second element has a partially spherical member with an outer surface shaped to mate with the outer surface of the partially spherical member of the first element. In a preferred embodiment, the first element has a partially spherical member with a convexly shaped outer surface, while the second element has a partially spherical member with a concavely shaped outer surface.

It has been found that the joint surface replacement system of the present invention offers numerous advantages. For example, the joint surface replacement system is formed from low-mass components which eliminates breakage, bulk and excessive weight. The joint surface replacement system replaces only the area of anatomic cartilage by size and function and provides full range of motion in all three planes. The joint surface replacement system also completely eliminates detritic synovitis.

Other details of the joint surface replacement system of the present invention as well as other objects and advantages attendant thereto are set forth in the following detailed description and the accompanying drawings in which like reference numbers depict like elements.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DESCRIPTION OF THE PREFERRED EMBODIMENT(S)

In describing the preferred embodiment of the present invention, reference will be made herein to FIGS. 1-19D of the drawings in which like numerals refer to like features of the invention.

In describing the instant invention, reference is made herein to U.S. Pat. No. 5,683,466 describing clockwise rotational spikes, the entirety of which is incorporated herein by reference. The instant apparatus, systems and methods are directed to subchondral bone restructure and/or replacement. The various implant screws disclosed herein, and described in relation to FIGS. 1-18, each have anti-rotation bone grips on a surface thereof for fixation to provide increased stability and anti-rotation once secured into bone. Additional improvements of the instant screws that provide ridged fixation and improved stability resulting in anti-rotation of the screws once within the bone include, but are not limited to: scalloped underside protrusions of the screw; curved radius edge; v-shaped bone contact side; threaded or non-threaded expandable tri-prong stem fixation anchor; counterclockwise positioned gripping protrusions; angled or curved threads on the screw stem; a threaded counter-bore; a subchondral bone growth disc residing at the underside of the screw; a subchondral bone growth coating on the screw and/or screw stem surfaces; and combinations thereof.

Figure 1:
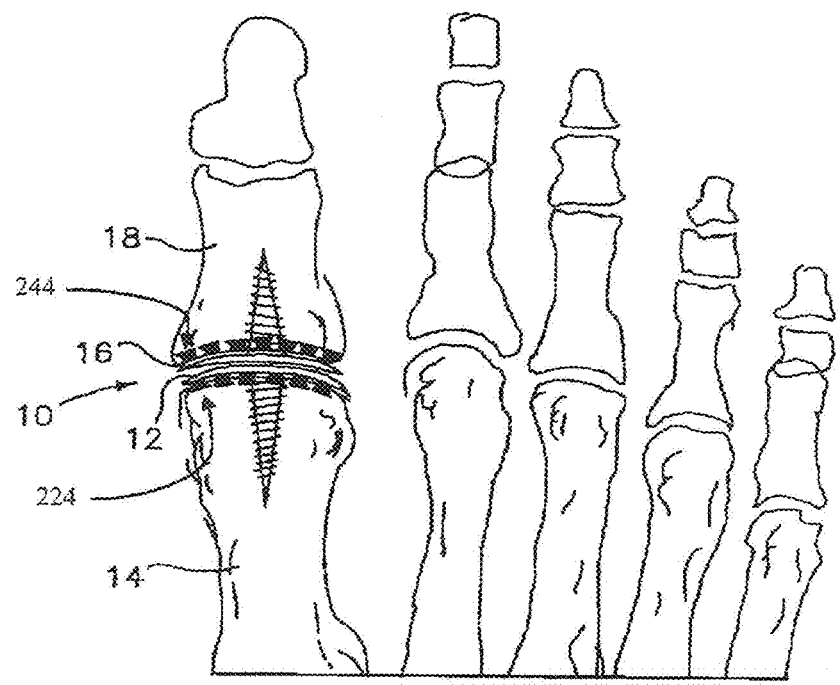
FIG. 1 illustrates a dorsal-plantar view of a human foot showing a total first metatarsal phalangeal joint articular surface replacement using the joint surface replacement system of the present invention.
Figure 2:
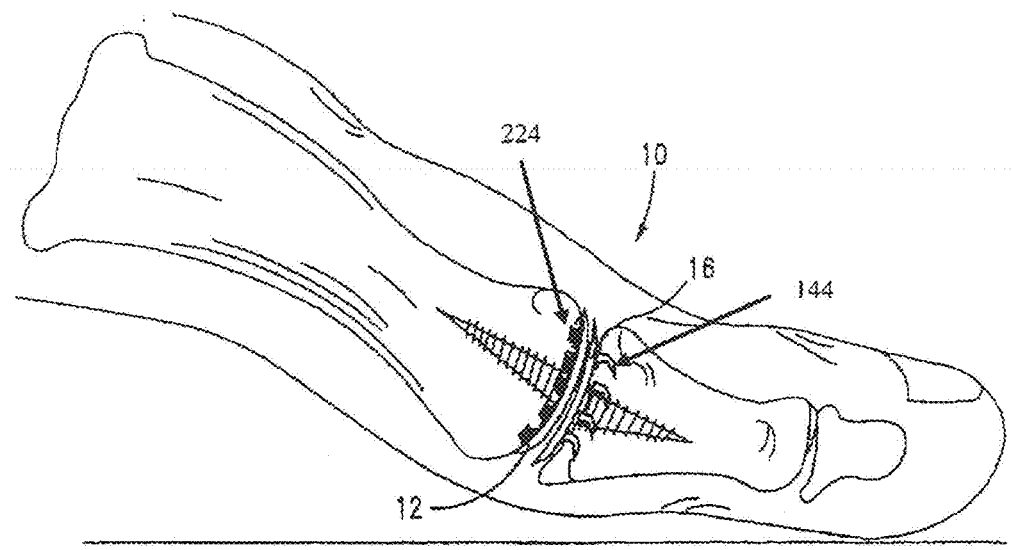
FIG. 2 illustrates a sagittal view of the foot of FIG. 1 showing the joint surface replacement system of the present invention.

Referring now to the drawings, FIGS. 1 and 2 illustrate a total first metatarsal phalangeal articular surface replacement using one or more joint surface replacement apparatus, systems and methods of the invention. In accordance with one or more embodiments, various joint surface replacement systems 10 of the invention are shown. These systems include a first component 12 implanted into a first bone 14 and a second component 16 implanted into a second bone 18. The implant components 12, 14 and system 10 replaces only cartilaginous surface areas and facilitates functioning to the original anatomic structures.

Figure 3A:
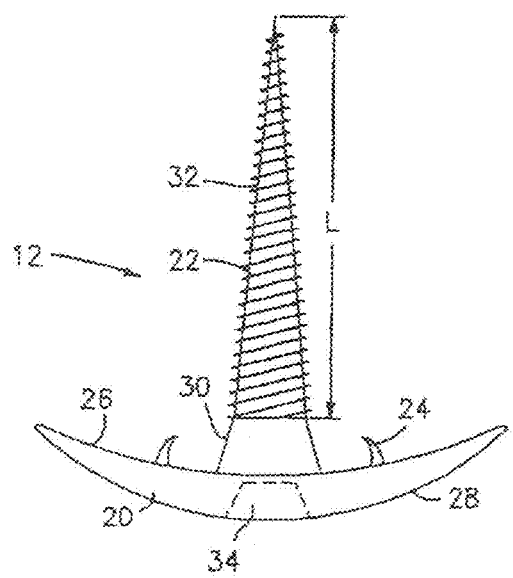
FIG. 3A illustrates a side view of a first component of the joint surface replacement system of the present invention.
Figure 3B:
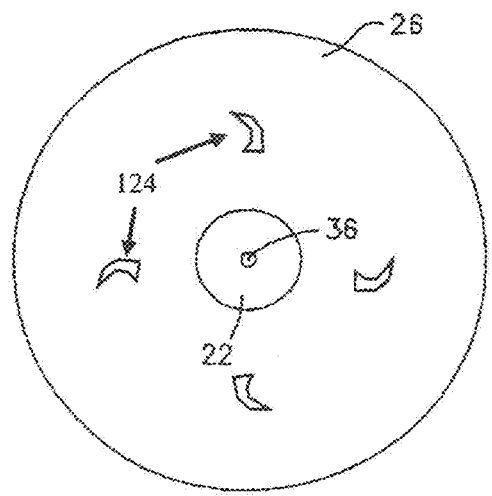
FIG. 3B illustrates an end view of the first component of FIG. 3A.

Referring to FIGS. 3A-3B, the first component 12 is a single-body structure having a partially spherical, tapered head piece 20 for covering the bone and functioning as an articular surface. The single-body structure also includes an integrally formed cancellous screw stem 22 and a plurality of anti-rotation locking bone grips 24 integrally formed on the interior side 26 of the head piece 20. The interior surface 26 and the exterior surface 28 of the head piece are each preferably convexly shaped. In one or more embodiments the two surfaces 26, 28 may have different radii so as to form a tapered head piece with the thinnest portion being at the outer periphery of the head. While not meant to be limiting, as an exemplary first component 12 of the invention the center of the head piece may have a thickness of about 2.0 mm while the outer periphery has a thickness of about 1.0 mm. The screw stem 22 is preferably centrally located with respect to the head piece 20.

Referring to FIG. 3A, the screw stem 22 has a non-threaded head portion 30 and a tapered threaded portion 32. The threaded portion has a length L sufficient to allow the first component to be inserted through the sub-chondral bone and into the medullary canal so as to substantially eliminate implant pistoning. Typically the length L will be from about 5 to about 15 millimeters. The non-threaded head portion 30 typically will have a length of about 3.5 millimeters. The thread on the portion 32 may have any suitable thread pattern and any suitable pitch.

The head piece 20 may be provided with a centrally located geometric shaped bore 34 at the top exterior surface 28 thereof. In one or more embodiments the bore 34 may be a hexagonally shaped, tapered bore 34. A reamer tool 100 of the invention, as shown in FIGS. 10A-10C, 14A-14C and 15, includes a mating protrusion at an end thereof that fits into the bore 34 opening for installing and removing the first component into and from bone. The head piece 20 is dimensioned to allow it to fully cover the end of the bone in which it is inserted.

Referring to the drawings, the plurality of anti-rotation locking bone grips 24 are radially spaced around and on the interior side 26 of the head piece 20. In accordance with one or more embodiments, the anti-rotation locking bone grips 24 may include a plurality of counterclockwise positioned gripping protrusions 124 (see, e.g., FIGS. 3B and 4B), a plurality of scalloped edges 224 (see, e.g., FIGS. 5-8C), inwardly angled grooved and scalloped bone grips 324 (see, e.g., FIGS. 12A-13B), angled or curved threads 400 on the screw stem (see, e.g., FIGS. 5-9C and 12A-13B), or any combination thereof.

As an alternative as shown in FIG. 3A, the bone grips may be angled inwardly in relationship to the threads 400 of the screw stem. The inwardly angled bone grips allow solid fixation by a compression press fit, thereby eliminating lateral stress forces in the transverse plane and rotational forces in the frontal plane. Preferably each bone grip has a length of about 2.0 mm.

Referring to FIG. 3B, the instant bone grips 24 may include counterclockwise positioned anti-rotation hook-shaped bone gripping protrusions 124 that are radially spaced about the center 36 of the head piece 20. Each of these bone gripping protrusions 124 may be spaced within the inner two-thirds of the bone in which the component is to be implanted, preferably from about 3 to about 4 mm from the center 36. The number of bone counterclockwise bone gripping protrusions 124 residing on the interior side 26 of the head piece 20 may vary depending upon the size of the first component implant 12 and/or the bone into which it is being inserted. It should also be appreciated that the placement of these counterclockwise bone gripping protrusions 124 may vary, and may be located at various positions on the interior side 36 including, for instance, equidistant from one another, in a circular pattern, in offset non-circular patterns, in rows or columns, and the like.

Figure 4A:
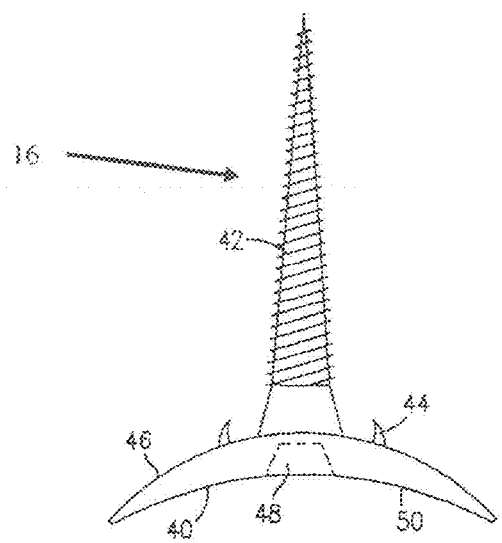
FIG. 4A illustrates a side view of a second component of the joint surface replacement system of the present invention.
Figure 4B:
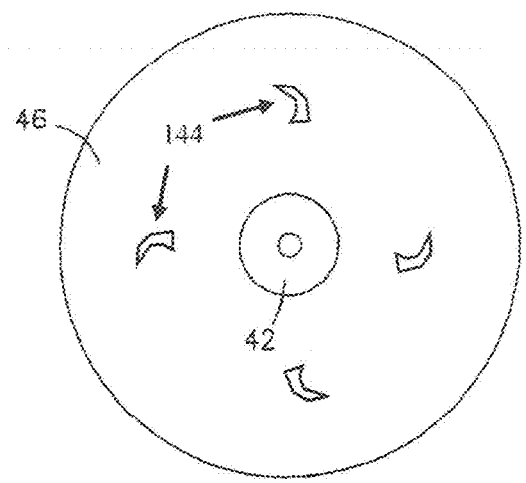
FIG. 4B illustrates an end view of the first component of FIG. 4A.

As shown in FIGS. 4A-4B, the second component 16 may also include a plurality of anti-rotation locking bone grips 44 radially spaced around and on the interior side 40 thereof. The second component 16 has a uni-body (single bod) construction with a partially spherical, tapered head piece 40, a centrally positioned cancellous screw 42 and a plurality of locking bone grips 44 radially spaced around and on the interior side 46 of the head piece 40. The head piece 40 differs from the head piece 34 of the first component 12 only by its shape. As shown in FIGS. 4A-4B, the head piece 40 has concavely shaped interior and exterior surfaces 46 and 50 respectively so as to allow the head piece 40 to mate with the head piece 34 and provide motion in all three planes. As before, the inner and outer surfaces 46 and 50 are formed by different radii so as to form a tapered construction having its thinnest portion at its outer periphery.

Figure 5:
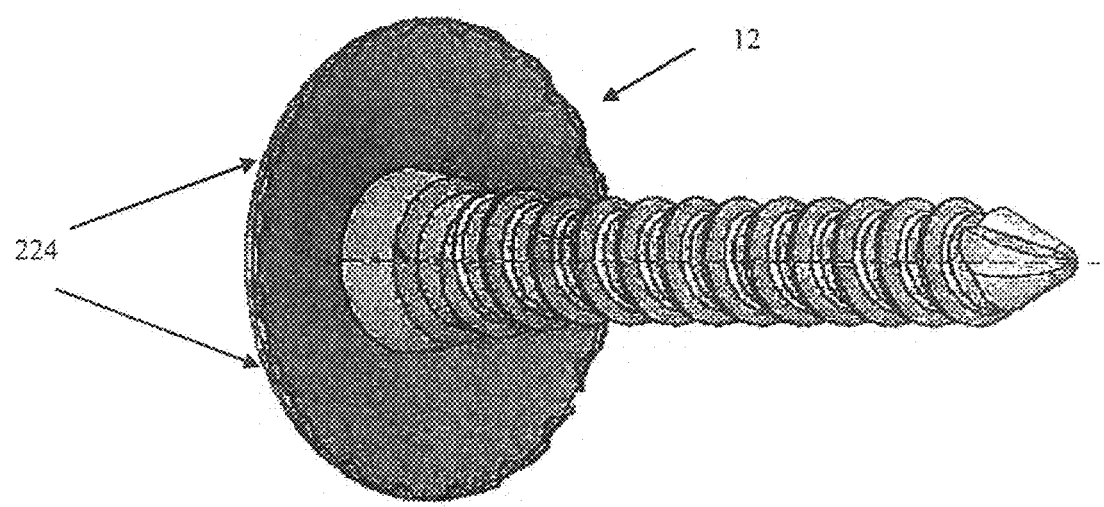
FIG. 5 illustrates a side perspective view of a screw component in accordance with one or more embodiments of the present invention.
Figure 6:
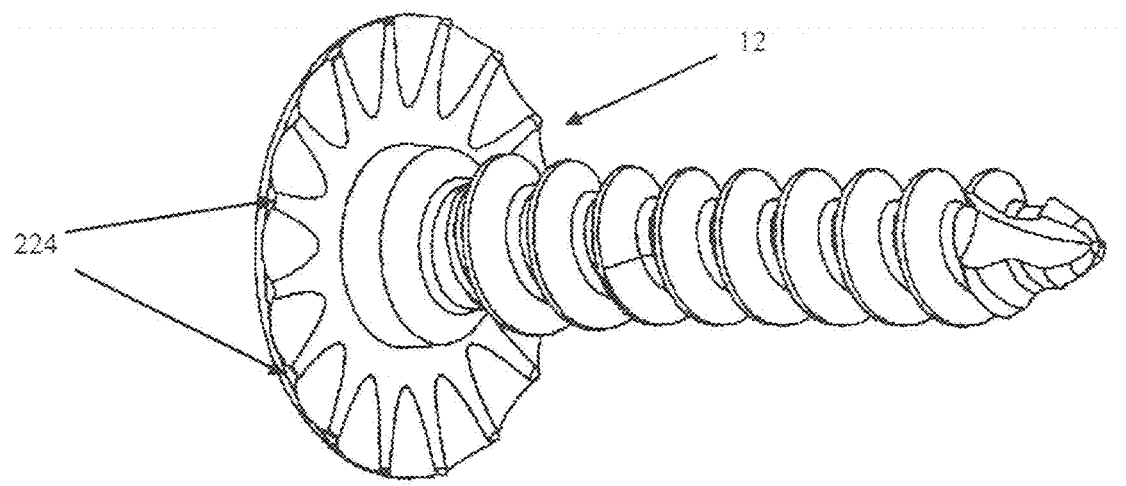
FIG. 6 illustrates a side perspective view of another screw component of the present joint surface replacement systems.

In one or more other embodiments the anti-rotation locking bone grips of the invention may include a plurality of scalloped edges 224 residing along a periphery of the interior side 26 of the head piece 20 of first component 12, and/or along a periphery of the interior side 46 of the head piece 40 of second component 16. FIGS. 5 and 6 show different side perspective views of various first component parts 12 of the invention having scalloped edges 224. These serrated and/or scalloped ridges/edges 224 at the interior side 26 of the head piece 20 of the screw prevent screw rotation.

The various perspective views of FIGS. 7A-8D show more details of the scalloped edges 224. These scalloped edges 224 may be serrated or non-serrated to prevent rotation once within the bone. In one or more embodiments the scalloped edges 224 may be serrated scalloped edges that fixate into the bone upon rotation and insertion of the screw into bone (via reamer tool 100) to provide a secure and non-rotatable screw within the bone. These serrated scalloped bone grip edges may be angled counterclockwise to further prevent counterclockwise rotation that may potentially undesirably loosen the joint surface replacement system. The serrated scalloped bone grip edges 224 reside entirely around the edges of the screw cap surface at edges thereof (e.g., 360-degrees) to a depth ranging from about 0.5 mm to about 1 mm deep. In certain embodiments the serrated scalloped bone grip edges 224 may be used at certain locations and based on indications of bone conditions.

Figure 9A:
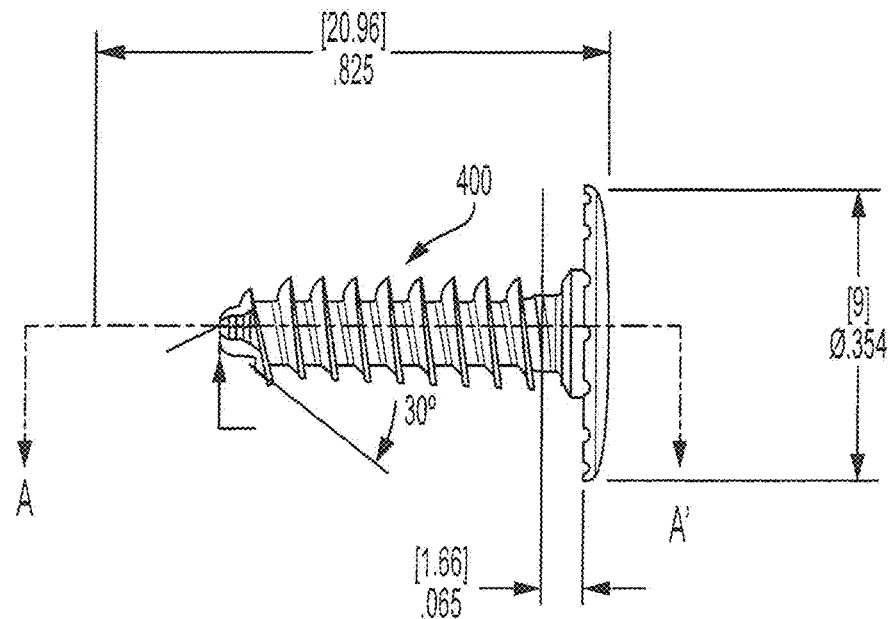
FIGS. 9A-9D illustrate details of the screw components in accordance with various embodiments of the invention.
Figure 9B:
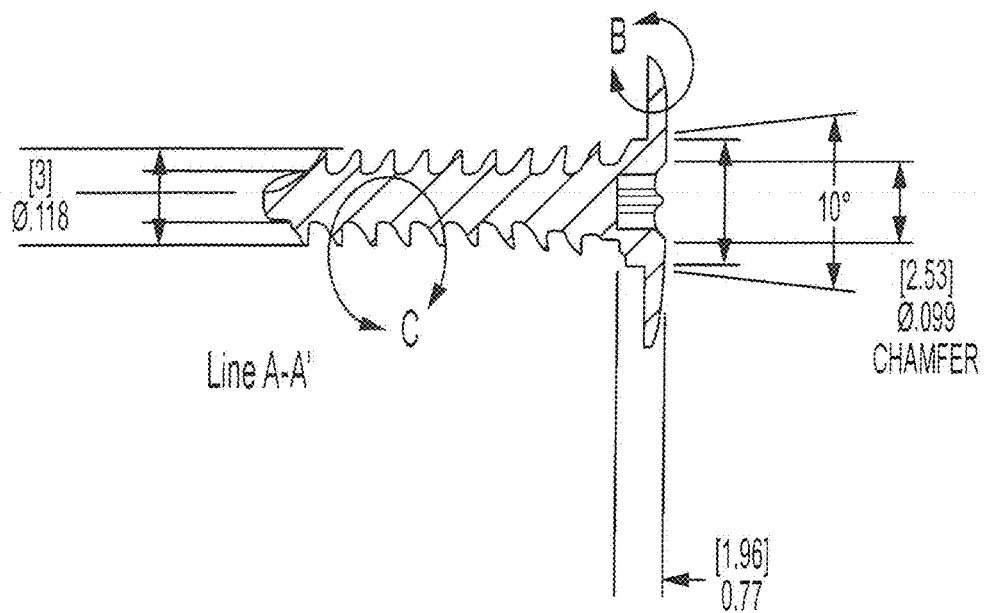
Figure 9C:
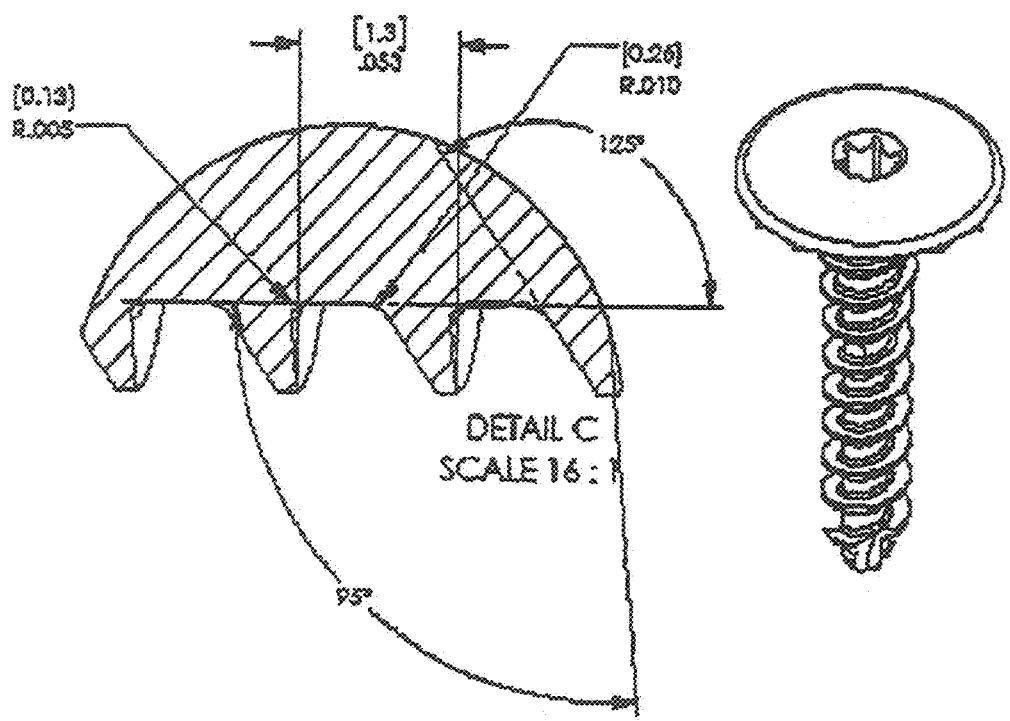
Figure 9D:
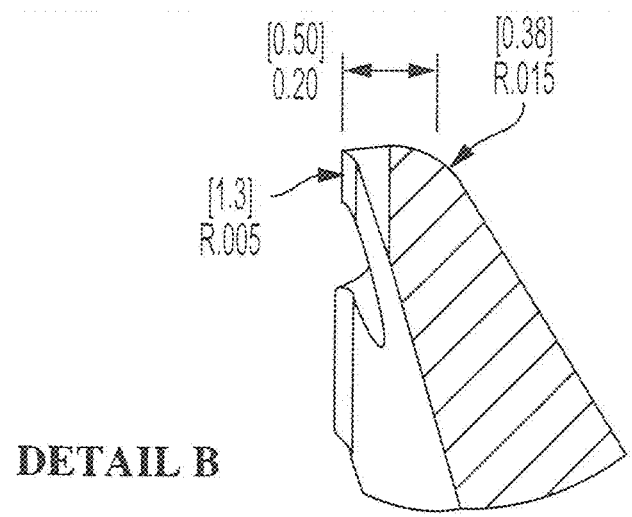
Figure 10A:
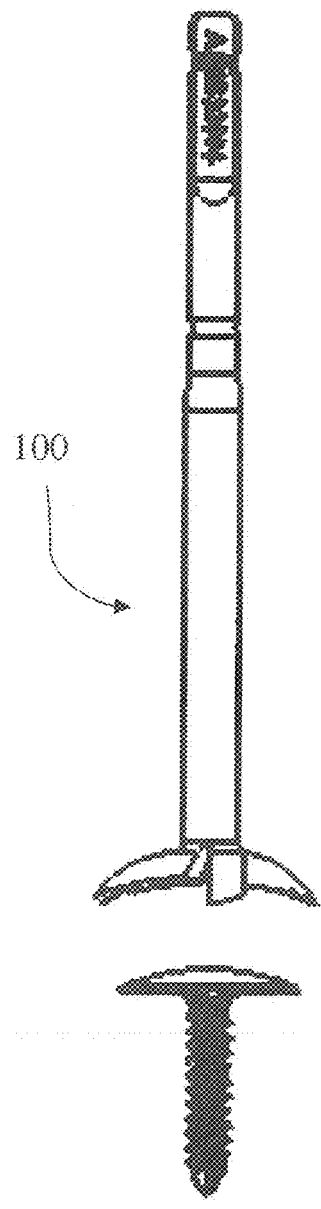
FIGS. 10A-10C illustrate various perspective views of a reamer tool used for application of the screw components of the invention.
Figure 10B:
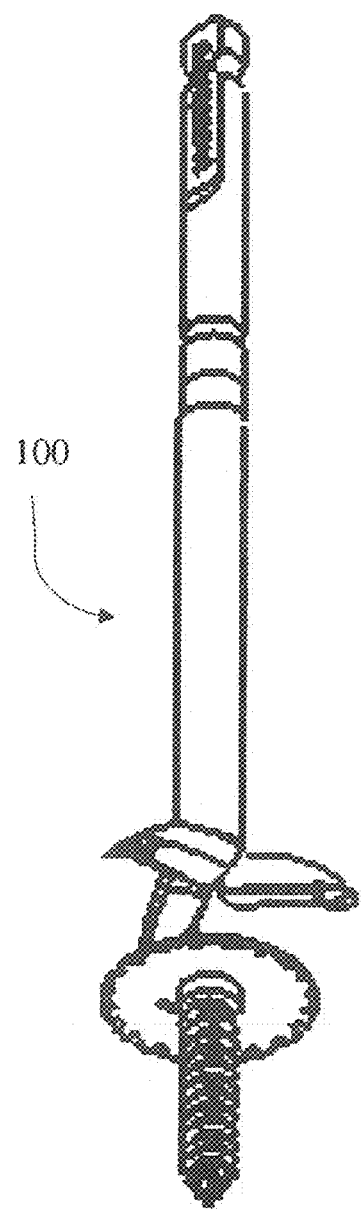
Figure 10C:
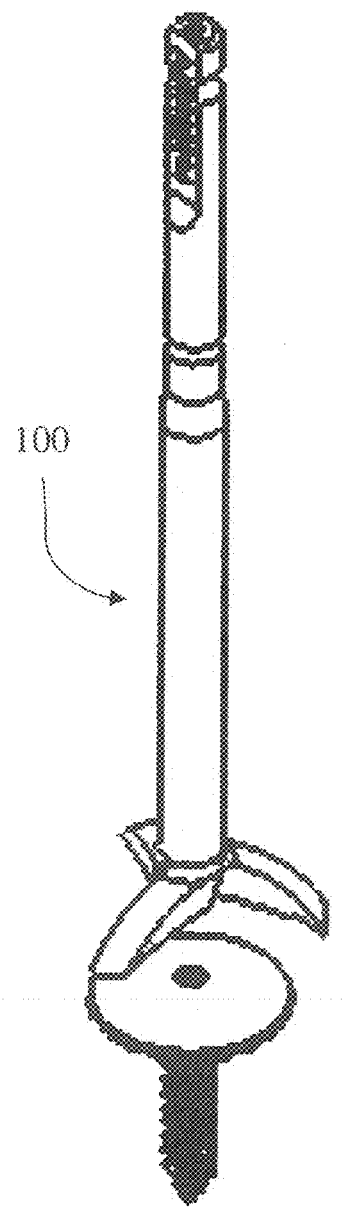

Referring to FIGS. 9A-9D various detailed angles and features of the instant screws 12, 16 are shown. FIG. 9A depicts the curvature of the inwardly sloped threads 400 of the screw stem, along with the angles thereof, while FIG. 9B shows the stem along line A-A' in FIG. 9A. The exploded view sections "C" and "B" are further depicted in FIGS. 9C and 9D, respectively. Referring to FIG. 9D, the entire outer peripheral radius edge of the screw head (i.e., the entire 360-degrees thereof) may have 90-degree curved sharp edges that engage subchondral bone upon affixing and tightening the screw therein. These 90-degree curved sharp edges hold the instant joint surface replacement firmly into the subchondral bone with improved and increased stability to prevent lateral shear and weight bearing forces from jarring the screw loose. It also transfers these forces off of the threaded screw stem, thereby preventing the threaded stem from loosening or backing out from counter rotation. Furthermore, downwardly extending 90-degree curved sharp edges prevent any articular interference of the instant subchondral bone replacement allowing it to function efficiently and without complications.

FIGS. 12A-14C show alternate embodiments of the instant screws having a plurality of anti-rotation locking bone grips. As shown the anti-rotation bone grips may comprise a plurality of grooved, scalloped channels 324 that allow for bone ingrowth to grow therein. While the drawings depict the instant grooved, scalloped channels 324 on screw 12, it should be appreciated that like grooved, scalloped channels 344 may be provided on the opposing or mating screw 16. These grooved, scalloped channels 324 may have different shapes and sizes as shown in FIGS. 13A and 13B. They also may reside at various locations along and around the surface of the head portion 20, 40 of the instant screws. By allowing bone ingrowth to occur within these grooved, scalloped channels 324, the occurrence of counter rotation or backing out of the threaded stem of the implant (i.e., "loosening of the screw") is drastically reduced as compared to the clockwise rotational spikes. The grooved, scalloped channels 324 of the invention provide improved rigid fixation.

While the various plurality of anti-rotation bone grips (i.e., 124/144, 224/244, 324/344) are described herein with respect to each other, it should be appreciated that the instant screws 12, 16 may be provided with any combination thereof. For instance, FIG. 2 shows screw 12 having scalloped edges 224, while screw 16 has counterclockwise protrusions 144. It should also be understood that a single screw 12 or 16 may have a combination of the instant anti-rotation bone grips (i.e., 124/144, 224/244, 324/344) provided on surfaces thereof for additional anti-rotation or prevention of screw loosening.

Figure 11:
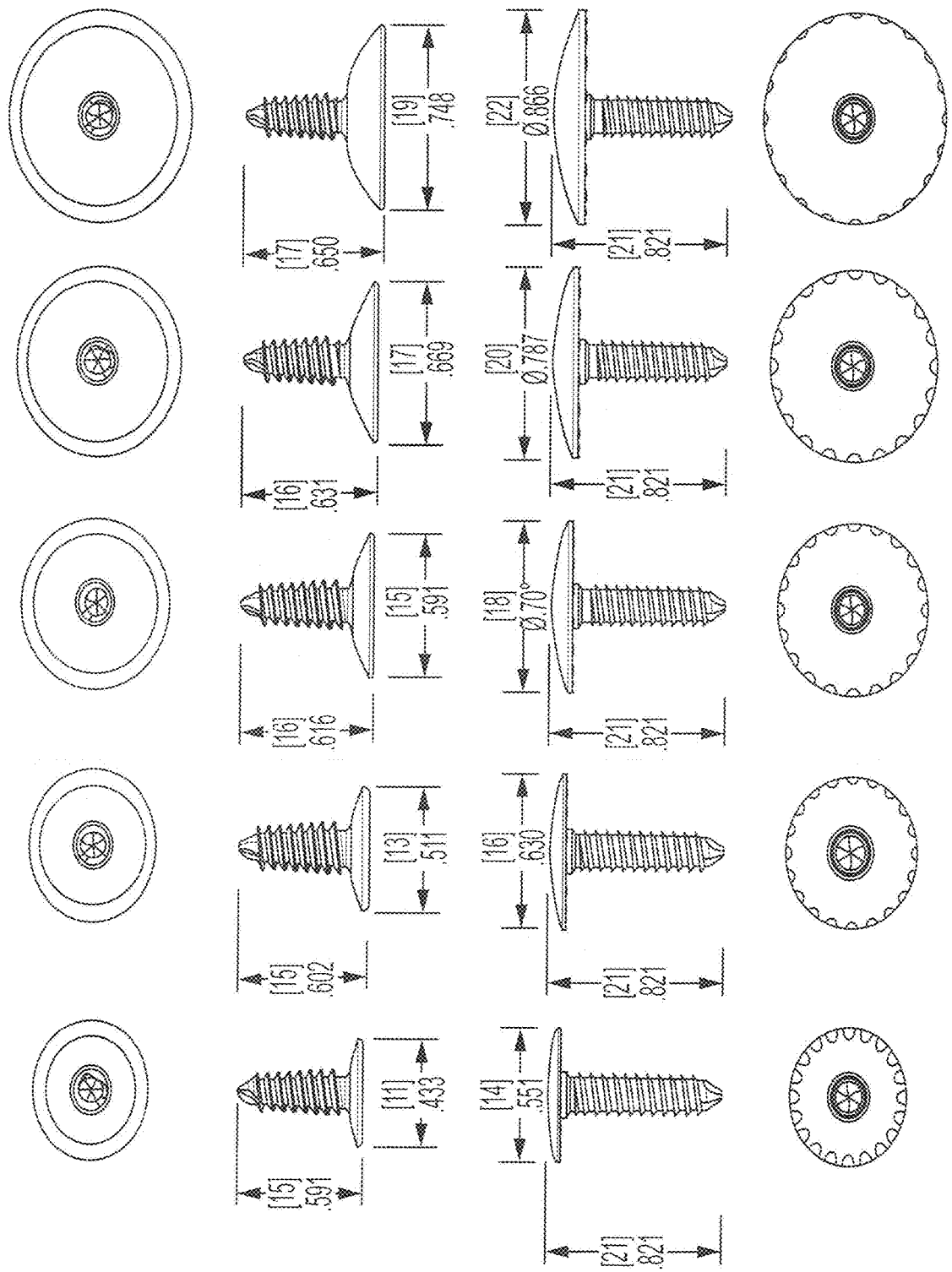
FIG. 11 illustrates the various sizes the first and second screw components of the invention may be provided with depending upon application thereof.
Figure 12A:
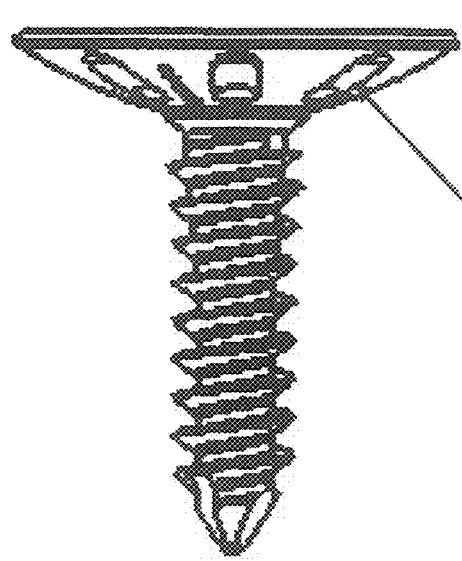
FIGS. 12A-13B illustrate different perspective views of the other screw components in accordance with various other embodiments of the invention.
Figure 12B:
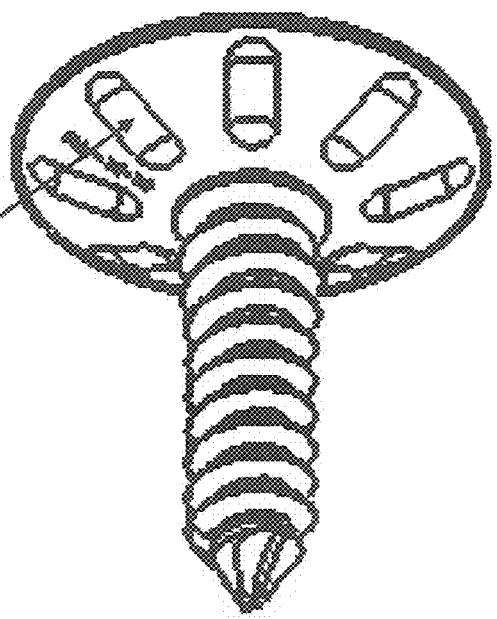
Figure 12C:
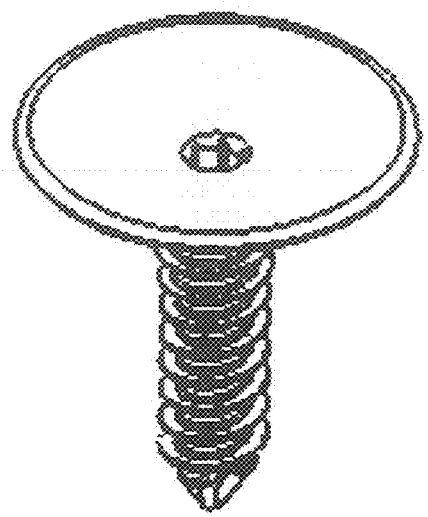
Figure 12D:
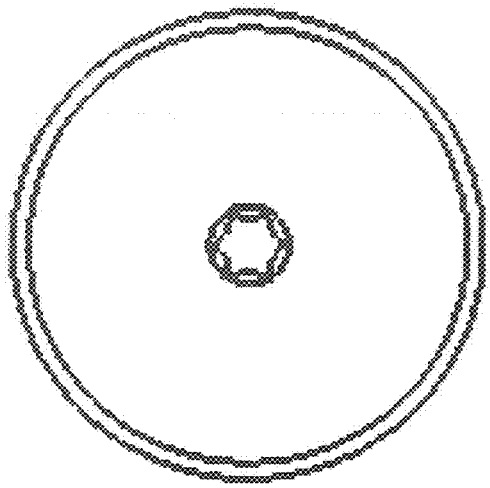
Figure 13A:
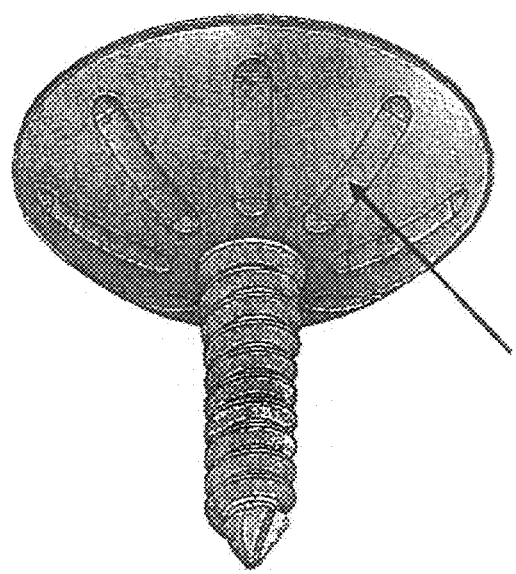
Figure 13B:
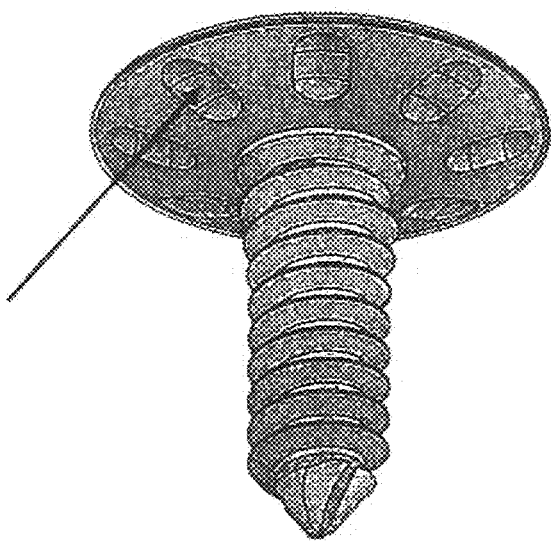

Referring to FIG. 11, the present screw components 12, 16 may be provided with a variety of different dimensions suitable for intended purposes. The components 12 and 16 may also be interchangeable, and are preferably formed from low-mass materials. For example, the components may be formed from chromium alloys such as a chromium cobalt alloy, titanium, a titanium alloy or stainless steel. The use of these materials eliminates breakage, bulk and excessive weight—major contributory factors to increased lateral shearing forces, the leading cause of decreased longevity and failure.

In a preferred embodiment of the present invention, the interior surfaces 24 and 46 of the head pieces 20 and 40 are coarsely finished to allow for boney ingrowth and to facilitate fixation. Additionally, each of the bone grips 24 and 44 are provided with coarse surfaces which also allow for bone ingrowth and to facilitate fixation to the bone.

In one or more embodiments of the invention, each screw stem may be provided with angled or sloped cancellous threads 400 ranging in size from about 1.5 mm to about 7.5 mm. It should be appreciated that the size will vary depending upon the joint application for various sized joints. The angled cancellous threads may be provided at both sides of the joint when necessary. The barrel of the screw stem may have a barrel that is angled at about 10 degrees and fully threaded. The screws also provide increase stability in view of the widening thereof and threaded counter-bore.

The thickness of the instant "joint surface replacement" implant system may be about 1 mm, and even up to about 3 mm thick. In certain embodiments an optimal thickness of about 2-4 mm may be required depending on surface materials needed for a total joint replacement or increased strength to all implants including HEMI implants. This additional or optional thickness is essential to bone lengthening, for correction of short first metatarsal or proximal phalanx. It may be in both the metatarsal and/or phalangeal components.

In one or more embodiments, the subchondral bone replacement systems and methods of the invention are non-weight bearing since the screws may be up to 20% smaller than outer circumference. The instant screw components 12, 16 may be composed of any material known to be used for joint "surface" replacement including, but not limited to, polyethylene, ethylene, polyurethane, polypropylene and other hard plastics, ceramics, titanium, cobalt chromium, stainless steel, SS 17-4ph hardened, and the like.

In certain embodiments, an optional two-piece joint replacement is provided, which may include a screw anchor or a snap-on articular surface implant. Various embodiments of the invention provides an optional cannulated implant, as well as a hexalobe/torx drive with recessed and/or chamfered edges.

Figure 19A:
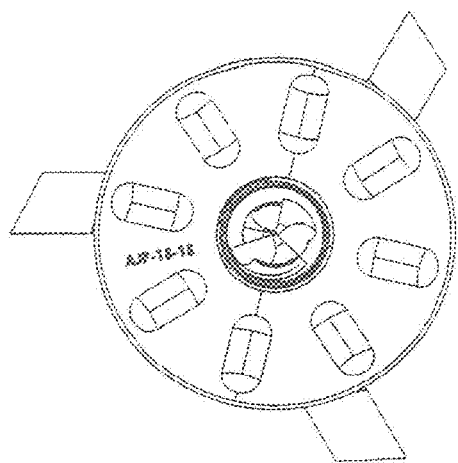
FIGS. 19A-19D illustrate different top down views of the installation of the present screws (FIGS. 19B and 19D) and bottom up views of the said screws (FIGS. 19A and 19C) showing expandable tri-prong stem fixation anchor of the invention.
Figure 19B:
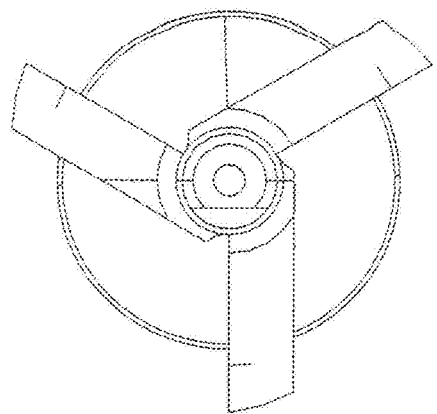
Figure 19C:
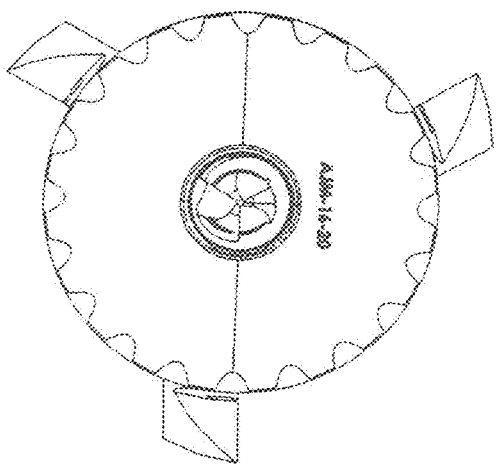
Figure 19D:
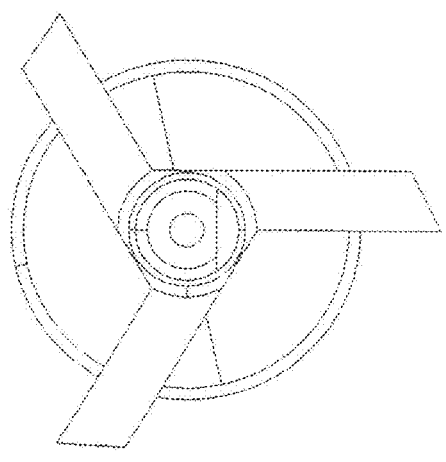

FIGS. 19B and 19D illustrate different top down views of the installation of the present screws using reamer tools 100 of the invention. FIGS. 19A and 19C illustrate bottom up views of the various screw components 12, 16 of the invention having threaded (or non-threaded) expandable tri-prong stem fixation anchor of the invention.

Figure 7A:
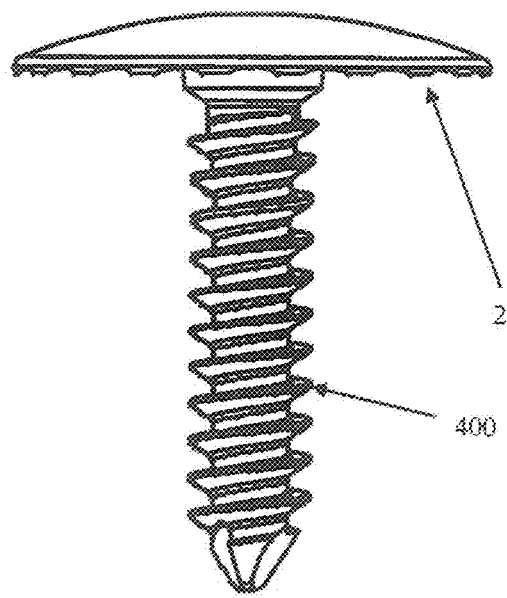
FIGS. 7A-8D are various views of the screw component of FIG. 5 in accordance with various embodiments of the invention.
Figure 7B:
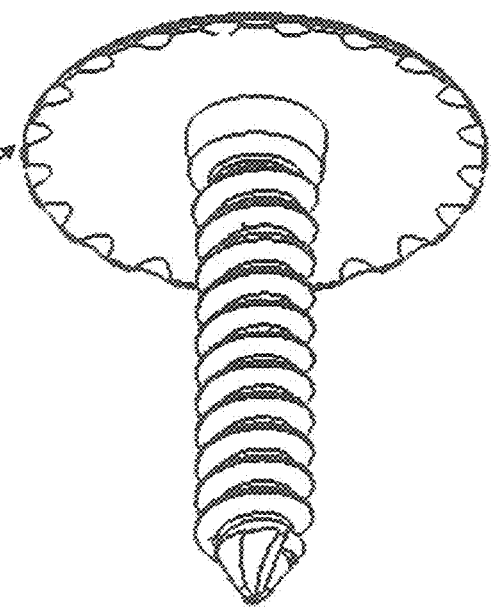
Figure 7C:
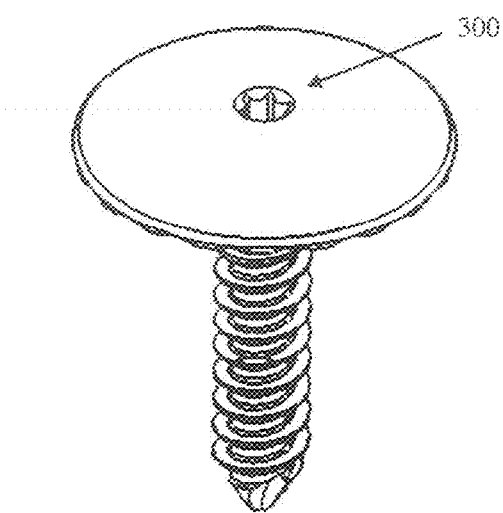
Figure 7D:
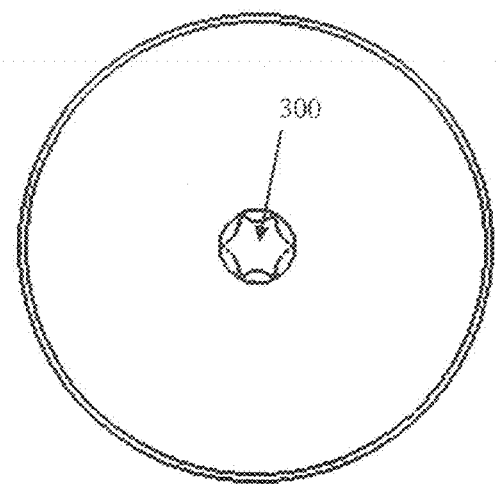
Figure 8A:
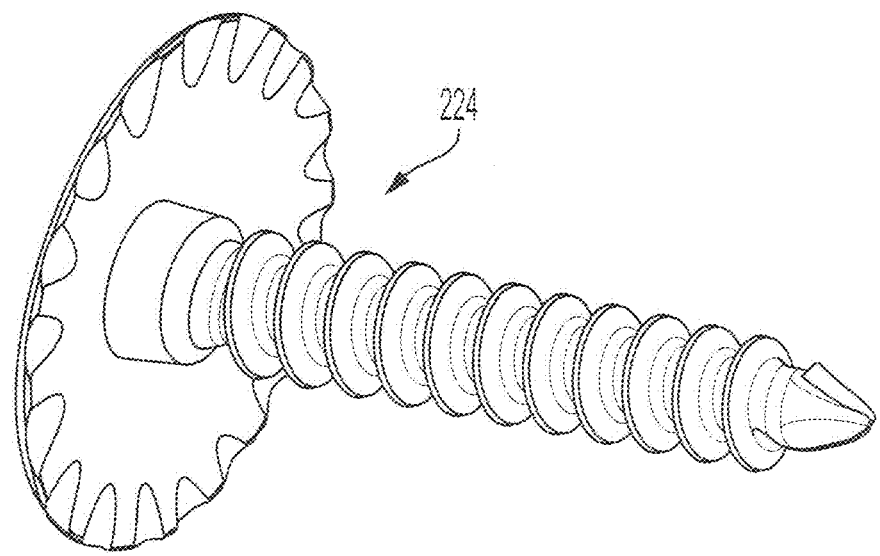
Figure 8B:
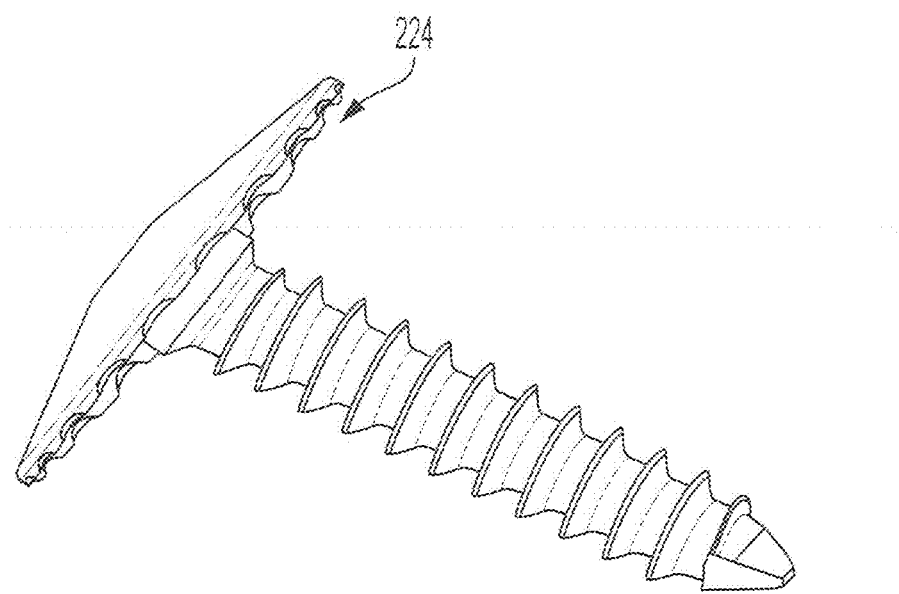
Figure 8C:
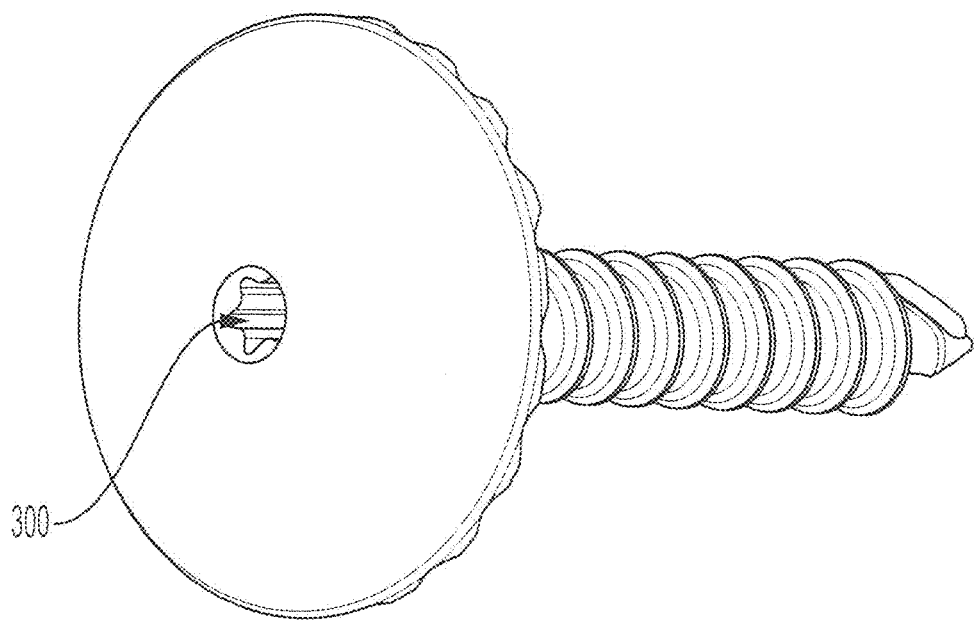
Figure 8D:
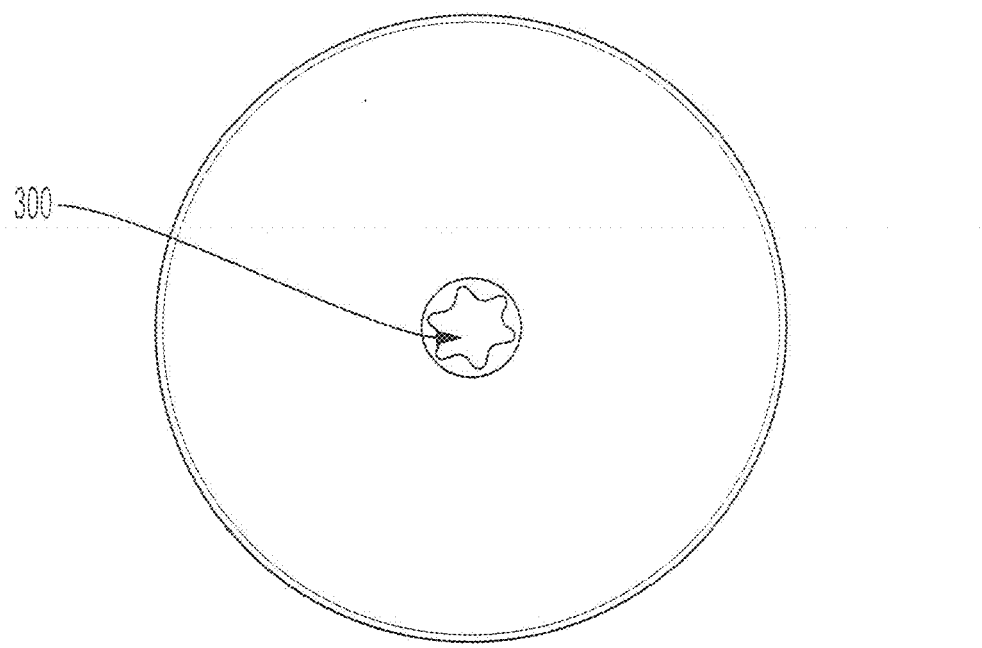

Also shown in FIGS. 7C-7D and 8C-8D is a non-tapered hexagonally shaped bore 300 centrally located on the exterior surface 28 of the head piece 20 (e.g., a hexagonally shaped, non-tapered bore as shown in FIGS. 7D and 8D). In these embodiments the reamer tool 100 has a hexagonally shaped drive portion to fit into the hexagonally shaped bore for securing and locking the screw into bone via the anti-rotation grips.

While the centrally located bore is shown as a hexagonally shaped, non-tapered bore, it should be appreciated that the screw bores may be internally tapered or non-tapered with a variety of different geometric configurations. For instance, the driver hole configurations and methods may be altered to be configured as a star shaped bore that accommodates a star shaped driver of a reamer tool 100. It has been found that the star shaped drive allows greater driver engagement, which in turn, minimizes slippage of the star shaped driver for screw insertion into bone, particularly size T10 or T15. The edges of the driver hole may also be rounded to eliminate potential interference with articular range of motion.

Still further, a cap cover may be provided for the driver hole. The cap cover may be a press fit cap cover. The driver hole cap cover prevents soft tissue and material build up within the driver hole. In one or more other embodiments the cap cover may be anywhere from 1-4 mm to maintain length of the bone. The cap cover may be a screw cap cover having a thickness from about 1 mm to 4 mm at the edge thereof.

Figure 17:
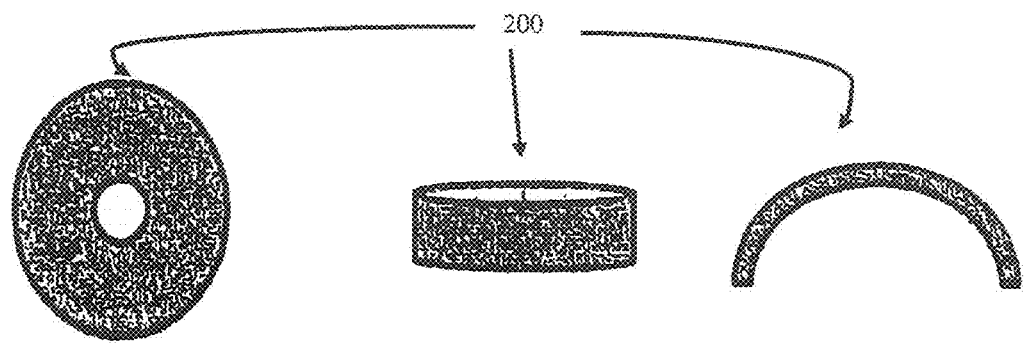
FIG. 17 illustrates different subchondral bone replacement apparatus of various embodiments of the invention.
Figure 18:
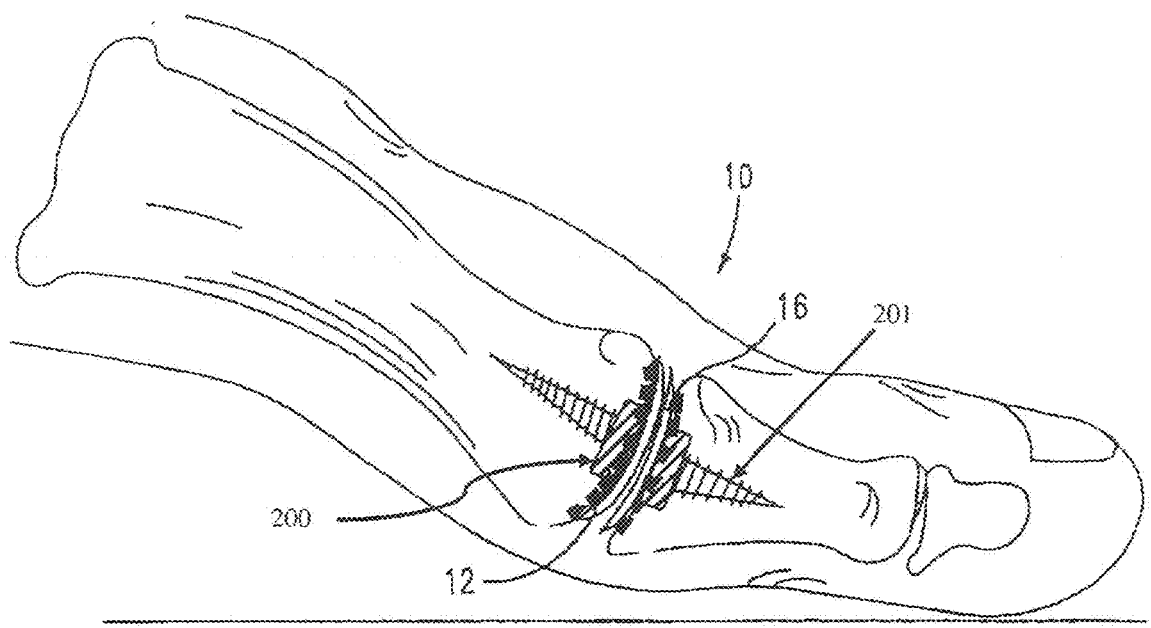
FIG. 18 illustrates a sagittal view of a foot showing the joint surface replacement system including the screws and subchondral bone replacement apparatus in accordance with one or more embodiments of the invention.

Referring to FIGS. 17 and 18, the present apparatus, systems and methods also include a subchondral bone replacement growth component. In one or more embodiments, the subchondral bone replacement growth component may be provided as a bone growth disc 200 (see, e.g., FIGS. 17 and 18), bone growth coating 201 (see, e.g., FIG. 18), or any other type of subchondral bone replacement growth apparatus.

In one or more embodiments the subchondral bone replacement may be in the form of a disc for insertion into an opening drilled in the bone. In other embodiments the subchondral bone growth replacement is a layer of a suitable material that coats the surface of the screw stem, the threads of the stem, the underside of the screw head, and/or any of the instant anti-rotation bone grips of the invention. One or more bone in-growth coatings may be applied to the entire screw and/or screw stem to provide improved and increased rigid fixation of the screw stem to bone via bone in-growth coating capabilities. The bone in-growth coating on the screw and/or screw stem increases the rigidity of the screw fixation and minimizes counterclockwise rotation that may potentially loosen the joint surface replacement system in all applications and joints.

These subchondral bone replacement systems and methods may be conjoined to the undersurface of all joint replacement systems and inserted together. For instance, the subchondral bone replacements are suitable for use when subchondral bone has been worn or destroyed by the arthritic process. The ability to replace this lost zone of subchondral bone will be beneficial for proper joint function and implant longevity, as well as provide shock absorption, increase bone length, and provide support to the instant joint replacement implants of the invention.

Referring to FIGS. 17 and 18, in one or more embodiments the subchondral bone replacement is a bone growth disc 200 added under the screws of the invention. In use, a bone and/or joint in need of repair is drilled out to a predetermined depth that accommodates both the screws of the invention and the subchondral bone replacement (e.g., subchondral bone replacement disc) placed under the screw. The subchondral bone replacement may be a part of or attached to the screw, or it may be separate therefrom. A portion of the bone material is removed, the subchondral bone replacement (e.g., subchondral bone replacement disc) is positioned in the drilled opening in the bone, followed by securing the screws of the invention therein. Again, the screw may have the bone growth disc on it. The method and system replace subchondral bone with the disc. In certain embodiments the subchondral bone replacement material may be provided in the opening in the bone and need to harden before inserting the screw therein. A preferred subchondral bone replacement may be a biological bone growth formulation. Synthetic bone growth formulations may also be used.

When the subchondral bone replacement is in the form of a disc, such disc may be about 3 mm to 5 mm thick. It will be a measured, formed, cannulated piece of hard, porous, synthetic bone as described, that will be manufactured, supplied and fitted underneath each sized implant, by diameter and radius when needed. The worn area of subchondral bone will be either cut flat or reamed in accordance to the proper radius of the implant. Depending on the amount of subchondral bone depth that has been destroyed, will depend the amount of depth or thickness needed to replace and order to fit the individual circumstance and implant. It will then be installed underneath and together with the implant, in one step. Over time, bony in-growth (osteoconductivity) will take place into this biocompatible synthetic material. Thickness/depth range for this replacement can be from 2 mm to 8 mm.

Materials suitable for use in the present subchondral bone replacement systems and methods have the ability to replicate and/or function as subchondral bone does, such that, it is able to act as bumper system (shock absorbing portion of the bone) that is highly significant to normal joint function. These materials also have the ability for the needed bone in-growth coatings to grow within the porous material used to replace the subchondral bone. The subchondral bone replacement systems and methods may be used in combination with any of the above systems and methods of the invention. The subchondral bone replacement may be composed of a filler material of a calcium phosphate cement formulation that provides osteoconductivity, biocompatibility, and excellent baseline strength.

The instant subchondral bone replacement systems are particularly suitable for loss of the cartilage zone due to destruction caused by arthritis. Calcium Phosphate and many other forms of porous, synthetic bone materials that are used for this purpose, act to fill "voids", and are made of proprietary formulations that provide "osteo-conductivity, biocompatability and excellent baseline strength.

Other embodiments of the invention are directed to altering the radius edges of joint surfaces replacements. Curved edges are added on the entire radius of all joint surface replacements to engage into the subchondral bone. These curved edges provide improved and increased stability and rigid fixation of the joint surface replacements to the subchondral bone, as well as resist weight bearing forces and forces potentially loosening the screw stem. The curved edges of the joint surfaces replacements also eliminate potential interference with articular range of motion.

Figure 14A:
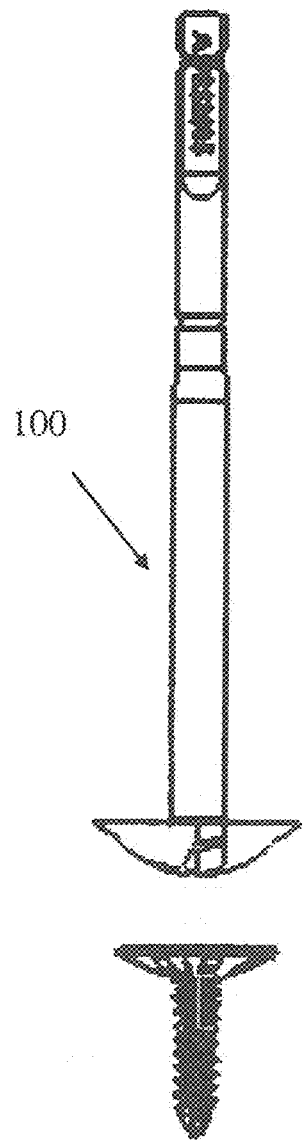
FIGS. 14A-14C illustrate various perspective views of a reamer tool suitable for use with the screw components shown in FIGS. 12A-13B.
Figure 14B:
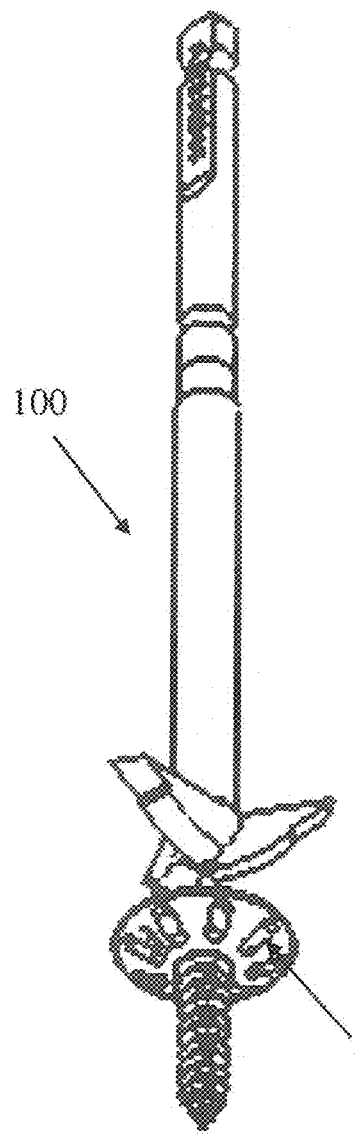
Figure 14C:
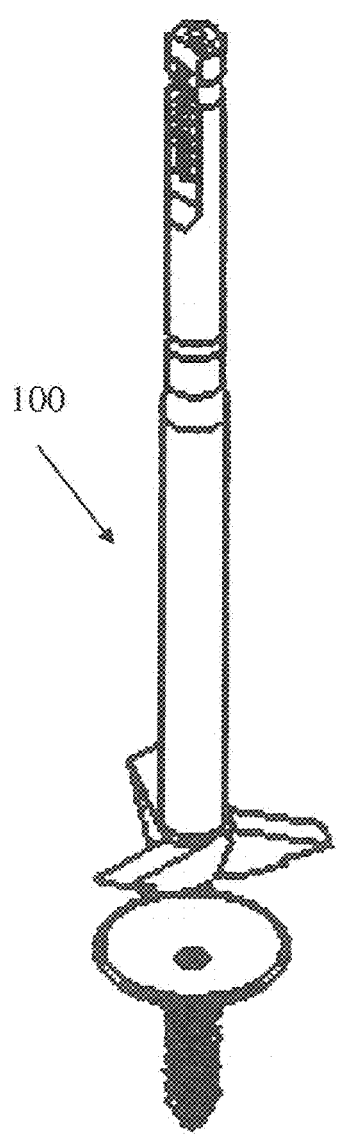
Figure 15:
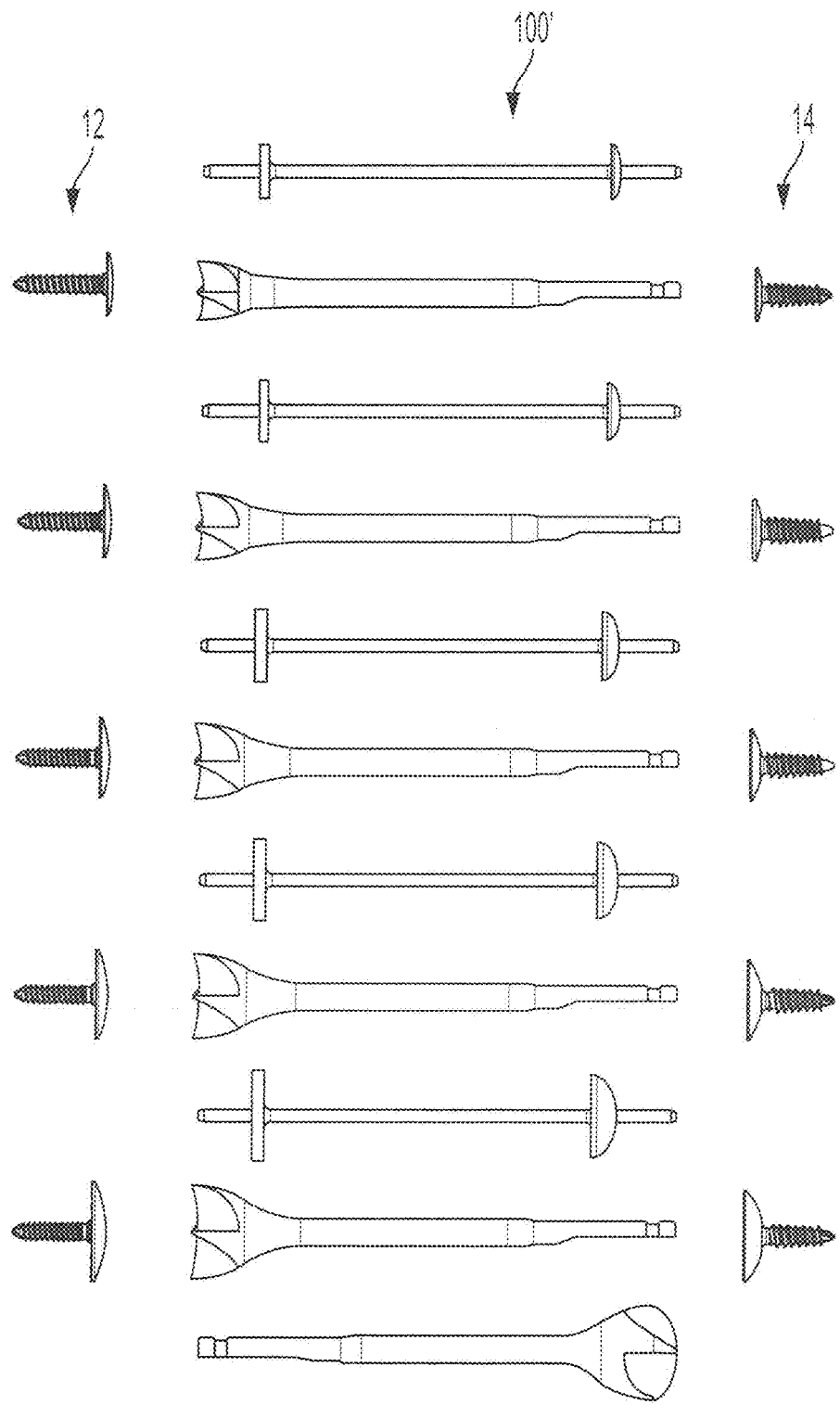
FIG. 15 illustrates different reamer tools and first and second screw components in accordance with various embodiments of the invention.
Figure 16A:
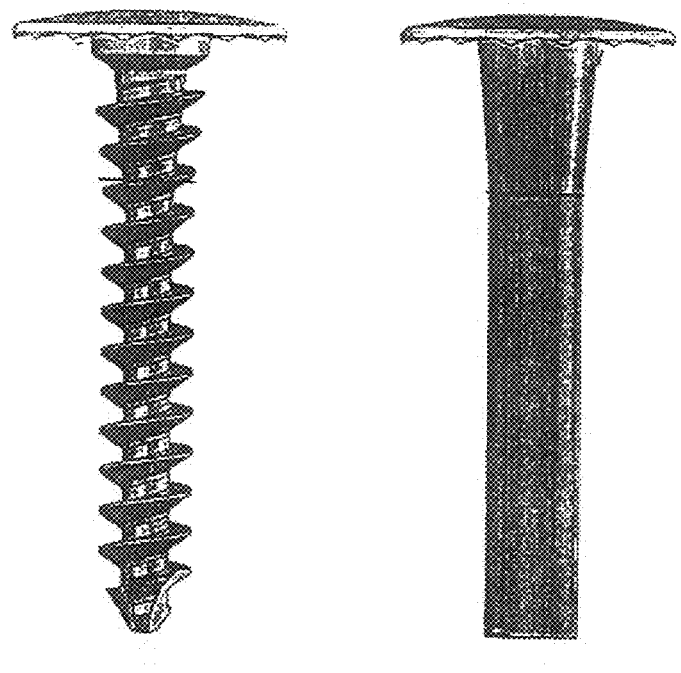
FIGS. 16A-16B illustrate different screw components in accordance with embodiments of the invention.
Figure 16B:
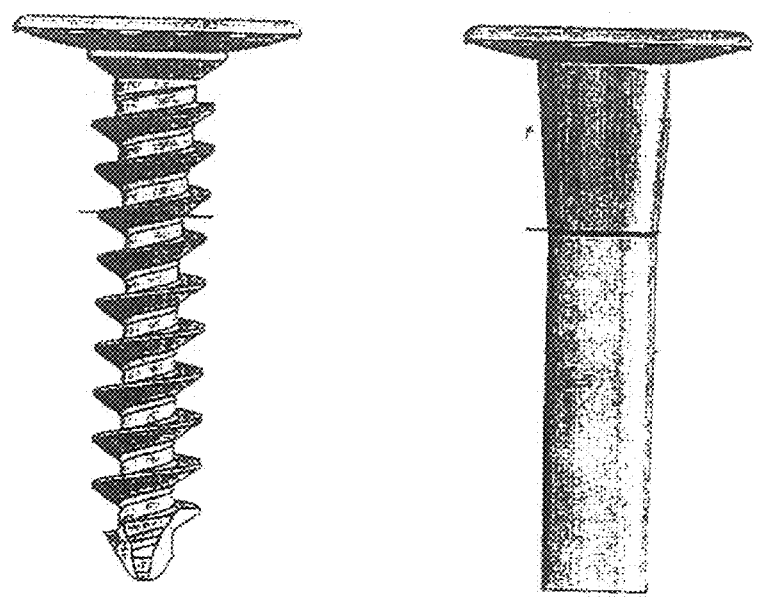

Referring to FIGS. 10A-10C, 14A-14C, and 15, the invention is also directed to in one or more embodiments reamer tools 100 for use with the various screws and driver hole configurations of the invention. A one-piece reamer tool instrument may be provided that combines the countersink instrument to the existing drill bit and surface grinder for enabling a single step process (rather than a two-step process) of prepping the end of the bone and for inserting all joint surface replacements, all within a single step. Referring to FIGS. 14A-14B, the reamer tools 100 include blades having staged double blades that enable the countersink and surface grind in a single step. The instruments may also include a star shaped driver instrument mounted at the opposite end, rather than using a separate hand standard hexagonally shaped driver, allowing significantly improved purchase power and minimizing slippage when inserting all joint replacement systems. The star shaped driver also provides the option for both power drive and hand installation, which is preferred in one or more embodiments. The one-piece instruments of the invention also save or decrease significant surgical time.

In accordance with one or more embodiments of the invention, the joint surface replacement system of the present invention may be installed by one or more of the following steps. It should be appreciated that other installation methods are also envisioned within the scope of the present invention.

A. Performing the standard surgical approach for arthroplasty to the involved joint to be replaced through skin, superficial and deep tissues preserving vital structures and tendons;

B. Entering capsular structures through the usual incisional approach, as to expose the involved joint surfaces for replacement;

C. Performing the standard peripheral "Chielectomy" procedure when appropriate or indicated, preserving the dorsal sack and all subchondral bone;

D. Prepping subchondral bone and worn joint surfaces with a mirror image drill bit, containing a central guide hole drill bit to maintain position while drilling. Marking the centermost portion of the joint surface and placing a guide hole bit on the marked central area and beginning drilling until the entire bore just approaches joint surface and "mildly scouring" worn joint surface until evenly and shaped with the bore bit;

E. Drilling guide hole (length times width) to appropriate size of stem of implant, and optionally drilling out additional space for subchondral bone replacement disc;

F. Counter sinking subchondral bone and at guide hole site, for the seating of the screw head barrel;

G. Tapping guide hole for thread size of implant stem;

H. Grasping the unibody articular surface replacement unit with forceps and placing screw stem (and optionally subchondral bone replacement disc) into tapped guide hole of bone. Utilizing reamer tool 100, screw in entire articular surface replacement into subchondral bone. Both screwhead barrel and anti-rotation bone grips engage snugly into subchondral bone during final quarter to half compression turns of insertion, and then turn counterclockwise to lock in anti-rotation bone grips;

I. Flushing entire wound with appropriate antibiotic flush;
   J. Approximate and close capsule, deep tissues and superficial tissues in layers with absorbable sutures. At this point, optional tendon lengthening or transfers may be performed when indicated;
   K. Closing skin in the usual fashion and apply post-operative dressing; and
   L. Maintaining early post-operative range of motion exercise and immediate ambulation after first three days.

The articular surface replacement is designed to further press fit and compress as weight bearing in normal activity continues post-operatively and throughout life.

The various joint surface replacement systems of the invention replace only the function of cartilage, not the function of a metatarsal, phalangeal, femoral or humeral head. The partially spherical shape to the head pieces serves to replace the area of anatomic cartilage by size and function. The angled thread, cancellous screw stem of each component eliminates pistoning forces and wearing of the inner cortical wall which leads to slippage and failure. The screw stem also allows easy removal when indicated and provides reliable stability and compression.

The taper to the outer spherical screw head barrel allows each component to be anchored to the bone via insertion and joint use compression over time to press fit into bone. It also eliminates lateral shearing forces in both the transverse and sagittal planes, thus relieving the entire screw stem from abnormal forces. The angled bone grips are designed at the same thread angle to engage sub-chondral bone during the last one-quarter turn of compression fit during insertion of each component. The bone grips further anchor the respective component to bone during joint use while weight bearing.

The joint surface replacement systems of the present invention are easily and clearly viewed on radiographs for observation and follow-up. The uni-body design of the system components allows a total view of the position of the entire implant.

The joint surface replacement systems are advantageous as the sub-chondral bone is left intact, thereby maintaining length and joint function of shock absorption and proprioception. Additionally, symmetry is preserved to that of the contralateral side. With respect to soft tissues, periarticular tendon, capsule and ligamentous structures are left intact during implantation of the system of the present invention. Soft tissue release and/or tendon transfer is utilized for joint alignment only, not for insertion of the implant articular replacement. Still further, the dorsal synovial sac may be preserved.

The system of the present invention eliminates detritic synovitis. No silicone, no silastics, no glues, no in-growth jackets and no grommets, which cause abrasion shards are required. Additionally, there are no shearing fractures of the stem or articular surface materials. Still further, encapsulations of microfragments, bone erosions and fibrosis are eliminated, unlike other implants.

The articular surface replacement system of the present invention may be inserted at time of an osteotomy and may be used for primary or secondary fixation of a head osteotomy. It eliminates the need to heal the first osteotomy before performing the implantation procedure.

If desired, the head pieces of the components may be fabricated from a material different from the material used for the screw stem and the bone grips. For example, they may be fabricated from ceramic materials or high density polyethylene for situations where a hemi-joint or partial joint implantation is to be performed. A hemi joint procedure would be performed where replacement of one articular surface alone is indicated. A partial joint procedure may be performed where only worn areas are to be replaced.

While the joint surface replacement system has been described in the context of replacing metatarsal phalangeal joints, it should be recognized that the same system could be used to replace other joints. For example, the system could be used to replace large joints such as hips and shoulders and digital joints of the fingers and toes.

It is apparent that there has been provided in accordance with this invention a joint surface replacement system which fully satisfies the objects, means and advantages set forth hereinbefore. While the invention has been described in combination with specific embodiments thereof, it is evident that many alternatives, modifications and variations will be apparent to those skilled in the art in light of the foregoing description. Accordingly, it is intended to embrace all such alternatives, modifications and variations as falling within the broad scope of the appended claims.

Thus, having described the invention, what is claimed is:

1. An articular surface replacement component sized and configured
   to be implanted into an end of a first bone comprising:
   an exterior articular surface defined by a concave head piece dimensioned to cover the end of the first bone, the concave head piece having an interior surface, an exterior surface, and an outer periphery connecting the interior and exterior surfaces;
   a plurality of recessed channel-shaped anti-rotation bone grips in the interior surface of the concave head piece that allow for ingrowth of the first bone therein;
   a centrally located stem extending from the interior surface of the concave head piece; and
   a plurality of threads extending around the stem
   wherein the interior surface of the concave head piece is a smooth contiguous surface area having the plurality of recessed channel-shaped anti-rotation bone grips recessed therein, each of the recessed channel-shaped anti-rotation bone grips having a length longer than a width and extending longitudinally in a radial direction from adjacent the outer periphery of the concave head piece at a first end of said length to adjacent the centrally located stem at a second end of said length,
   wherein the articular surface replacement component comprises a phalangeal component and the first bone comprises a phalangeal bone.

2. The component of claim 1 wherein the interior surface is a concave interior surface and the exterior surface is a concave exterior surface.

3. The component of claim 2 wherein the concave interior and exterior surfaces have different radii providing a tapered head piece with a thinnest portion residing at the outer periphery of the tapered head piece.

4. The component of claim 1 further including a centrally located driver hole on the exterior articular surface of the concave head piece for inserting the first component into the first bone.

5. The component of claim 1 wherein each recessed channel-shaped anti-rotation bone grip is a single radially-extending channel in the interior surface of the concave head piece extending from adjacent the outer periphery of the concave head piece to adjacent the centrally located stem.

6. The component of claim 1 wherein the channel-shaped anti-rotation bone grips reside in a circular pattern on the interior surface of the concave head piece.

7. The component of claim 1 wherein the channel-shaped anti-rotation bone grips have coarsely finished surfaces adapted to abut the first bone and allow ingrowth of the first bone into the channel-shaped anti-rotation bone grips to further solidify fixation to the first bone.

8. The component of claim 1 wherein the channel-shaped anti-rotation bone grips comprise a plurality of grooved, scalloped channels that allow for bone ingrowth to grow therein that provide solid fixation to the first bone.

9. The component of claim 1 wherein the channel-shaped anti-rotation bone grips are uniform in shape and size.

10. The component of claim 1 wherein the recessed channel-shaped anti-rotation bone grips are elongated recessed channel-shaped anti-rotation bone grips separated from one another by portions of the smooth contiguous surface area of the interior surface of the concave head piece.

11. The component of claim 1 wherein the channel-shaped anti-rotation bone grips have angled portions.

12. The component of claim 1 wherein the channel-shaped anti-rotation bone grips reside at various locations on the interior surface of the concave head piece.

13. The component of claim 1 wherein the centrally located stem is tapered.

14. The component of claim 1 wherein the centrally located stem has a non-threaded portion and a tapered threaded portion, the tapered threaded portion having a length sufficient to extend through intact sub-chondral bone and into the first bone's medullary canal.

15. The component of claim 1 wherein the component comprises a material selected from the group consisting of titanium, a titanium alloy, stainless steel and a chromium alloy.

16. The component of claim 1 further including at least a portion of the component is coated with a subchondral bone replacement in-growth coating.

17. The component of claim 1 wherein the concave head piece has an outer surface which forms a cartilaginous spherical articular surface and a coarsely finished interior surface for promoting boney ingrowth and thereby facilitating fixation.

18. An articular surface replacement component sized and configured to be implanted into an end of a phalangeal bone consisting essentially of:
   an exterior articular surface defined by a concave head piece dimensioned to cover the end of the phalangeal bone, the concave head piece having an interior surface, an exterior surface, and an outer periphery connecting the interior and exterior surfaces;
   a plurality of radially-extending recessed channel-shaped anti-rotation bone grips having coarsely finished surfaces in the interior surface of the concave head piece that allow for ingrowth of the phalangeal bone therein to solidify fixation to the phalangeal bone;
   a centrally located stem extending from the interior surface of the concave head piece; and
   a plurality of threads extending around the stem,
   wherein the interior surface of the concave head piece is a smooth, contiguous surface area having the plurality of radially-extending recessed channel-shaped anti-rotation bone grips recessed therein, each of the radially-extending recessed channel-shaped anti-rotation bone grips having a length and a width and extending longitudinally in a radial direction across the interior surface with a first end of said length being adjacent to the outer periphery of the concave head piece and a second end of said length being adjacent to the centrally located stem,
   wherein the articular surface replacement component comprises a phalangeal component.

\* \* \* \* \*